US006881214B2

(12) United States Patent
Cosman et al.

(10) Patent No.: US 6,881,214 B2
(45) Date of Patent: Apr. 19, 2005

(54) ABLATION TREATMENT OF BONE METASTASES

(75) Inventors: Eric R. Cosman, Belmont, MA (US); William Rittman, Lynnfield, MA (US)

(73) Assignee: Sherwood Services AG, Schaffhausen (CH)

( * ) Notice: Subject to any disclaimer, the term of this patent is extended or adjusted under 35 U.S.C. 154(b) by 159 days.

(21) Appl. No.: 10/260,446

(22) Filed: Sep. 27, 2002

(65) Prior Publication Data

US 2003/0040743 A1 Feb. 27, 2003

Related U.S. Application Data

(63) Continuation of application No. 09/584,877, filed on Jun. 1, 2000, now Pat. No. 6,478,793.
(60) Provisional application No. 60/138,961, filed on Jun. 11, 1999.

(51) Int. Cl.[7] ............................................. A61B 18/18
(52) U.S. Cl. ......................... 606/45; 606/49; 607/101; 607/102
(58) Field of Search ............................ 606/41, 45–50; 607/96–102

(56) References Cited

U.S. PATENT DOCUMENTS

| | | |
|---|---|---|
| 4,411,266 A | 10/1983 | Cosman |
| 4,565,200 A | 1/1986 | Cosman |
| 4,966,597 A | 10/1990 | Cosman |
| 4,993,430 A | 2/1991 | Shimoyama et al. |
| 5,029,588 A | 7/1991 | Yock et al. |
| 5,230,623 A | 7/1993 | Guthrie et al. |
| 5,267,994 A | 12/1993 | Gentelia et al. |
| 5,281,213 A | 1/1994 | Milder et al. |
| 5,323,778 A | 6/1994 | Kandarpa et al. |
| 5,330,518 A | 7/1994 | Neilson et al. |
| 5,334,193 A | 8/1994 | Nardella |
| 5,342,357 A | 8/1994 | Nardella |
| 5,348,554 A | 9/1994 | Imran et al. |
| 5,383,876 A | 1/1995 | Nardella |
| 5,409,000 A | 4/1995 | Imran |
| 5,409,006 A | 4/1995 | Buchholtz et al. |
| 5,433,739 A | 7/1995 | Imran |
| 5,458,597 A | 10/1995 | Edwards et al. |
| 5,462,521 A | 10/1995 | Brucker et al. |
| 5,472,441 A * | 12/1995 | Edwards et al. ............... 606/41 |
| 5,520,684 A | 5/1996 | Imran |
| 5,536,267 A | 7/1996 | Edwards et al. |
| 5,571,147 A | 11/1996 | Sluijter et al. |

(Continued)

FOREIGN PATENT DOCUMENTS

| | | |
|---|---|---|
| EP | 0310431 | 4/1989 |
| EP | 0608609 | 8/1994 |
| WO | WO 9428809 | 12/1994 |
| WO | WO 9604860 | 2/1996 |
| WO | WO 9618349 | 6/1996 |
| WO | WO 9629946 | 10/1996 |
| WO | WO 99/01074 | 1/1999 |

*Primary Examiner*—Roy D. Gibson

(57) ABSTRACT

Ablative treatment of metastatic bone tumors and relief of pain associated with metastatic bone tumors is achieved by heat ablation of the bone tumor or tissue near the bone tumor by an ablation probe. In one form the probe is an electrode coupled to a high frequency power supply to provide ablative heating of tissue proximate to an electrode that is placed in or near the bone tumor. Cooling of the electrode by fluid circulation from a cooling apparatus outside the patient's body may be used to enlarge the region of high frequency heating around the electrode. Image guidance of the electrode placement may be monitored by an imaging device. Tracking of the electrode by an image-guided navigator helps in placement of the electrode with respect to the configuration of the bone and bone metastasis. A set of tools accommodates biopsy and various shapes of electrodes according to clinical requirements. Several forms of electrodes, energy delivery and cooling apparatus and methods accommodate the specific objectives.

9 Claims, 5 Drawing Sheets

U.S. PATENT DOCUMENTS

| | | | |
|---|---|---|---|
| 5,647,871 A | 7/1997 | Levine et al. | |
| 5,662,111 A | 9/1997 | Cosman | |
| 5,735,847 A | 4/1998 | Gough et al. | |
| 5,775,338 A | * 7/1998 | Hastings | 128/898 |
| 5,792,146 A | 8/1998 | Cosman | |
| 5,848,967 A | 12/1998 | Cosman | |
| 5,849,011 A | 12/1998 | Jones et al. | |
| 5,921,992 A | 7/1999 | Costales et al. | |
| 5,951,546 A | 9/1999 | Lorentzen | |
| 6,006,126 A | 12/1999 | Cosman | |
| 6,106,524 A | * 8/2000 | Eggers et al. | 606/50 |
| 6,146,380 A | * 11/2000 | Racz et al. | 606/41 |
| 6,605,085 B1 | * 8/2003 | Edwards | 606/41 |

* cited by examiner

ABLATION TREATMENT OF BONE METASTASES

CROSS-REFERENCE TO RELATED APPLICATIONS

This application is a continuation of U.S. application Ser. No. 09/584,877, filed Jun. 1, 2000, now U.S. Pat. No. 6,478,793, which claims priority to and the benefit of U.S. Provisional Application Ser. No. 60/138,961, filed Jun. 11, 1999. The disclosures of each of these prior applications are hereby incorporated by reference in their entirety.

FIELD OF THE INVENTION

This invention relates generally to the advances in medical systems and procedures for prolonging or improving human life. More particularly, this invention relates to an improved method and system for destroying cancerous bone metastatic tumors and relieving pain symptoms caused by such tumors or metastatic disease.

BACKGROUND OF THE INVENTION

A very large percentage of all cancerous disease which spreads, or metastasizes, results in growth of metastatic tumors, called metastases, in the bony structures of the patient's body. In advanced metastatic bone disease, the patient experiences excruciating pain due to pressure of the tumor on surrounding nerves, tissue, and the innervation of the bone and endosteum or periosteum itself. The quality of the patient's life at this point can deteriorate quickly, and the levels of pain become intolerable.

The common methods of treating metastatic cancerous tumors include radiation therapy. Application of X-ray radiation therapy can slow the progression of bone metastatic cancer growth but usually cannot halt it. Moreover, some bone metastases are relatively unresponsive to radiation therapy. Another problem with radiation therapy is that it causes death of the bone marrow which produces the red blood cells that are vital to life. Therefore, only a limited amount of X-ray dosage can be given before critical destruction of bone marrow takes place. Another limitation of radiation therapy is that once it has been administered up to a certain dose level, further application of the radiation therapy typically is prohibited. This is to prevent overdosing of the surrounding normal tissue and organs in the patient. In sum, radiation therapy has a limited repeatability.

Radiation therapy also is a relatively complex and expensive procedure. Localization of the cancerous tumor with respect to the therapeutic X-ray beam may be difficult as a result of inaccurate patient positioning on an X-ray delivery device such as a linear accelerator (LINAC). To be effective, fractionated or repeated doses of radiation have to be given over a period of weeks or months. This is expensive in terms of equipment time and personnel costs, and can be inconvenient for a patient who is ill.

Localization of the metastatic tumor volume in the X-ray beam is a difficult technical problem which remains a challenge for radiation therapy. As a consequence of the indefiniteness of the tumor localization in the X-ray beam, larger margins of dosimetry must be given. This further puts at risk sensitive, normal tissue or organs that are nearby the bone and the bone tumor. Excess delivery of radiation to normal tissue can be very harmful with severe side effects and deterioration of the patient's condition and quality of life.

Chemotherapy is another method of treating bone metastases. This is a systemic treatment that can cause severe sickness in and inconvenience to the patient. Because of the toxicity of chemotherapy, the rest of the body's systems are put at risk. Moreover, the effectiveness of chemotherapy in targeting the bone tumor itself is limited.

The treatment of a primary benign bone tumor using a percutaneously placed radiofrequency electrode has been reported by Rosenthal, et al. in their paper entitled "Percutaneous Radiofrequency Treatment of Osteoid Osteomas," Seminars in Musculoskeletal Radiology, Volume 1, Nov. 2, 1997. A radiofrequency electrode was inserted into the small primary bone tumor and connected to a radiofrequency power source to heat the bone tumor so as to destroy it. A bone tumor which they destroyed was of a type called "osteo-osteoma," which is a relatively rare disease. They were successful in heating the osteo-osteoma tumor and destroying it completely in some cases. Osteo-osteomas are typically small tumors with a diameter of 1 to 2 centimeters. Rosenthal did not contemplate treating larger bone cancer or the painful condition they create.

It should be recognized that the theory behind and practice of radiofrequency (RF) heat lesioning has been known for decades, and a wide range of RF generators and electrodes for accomplishing such practice exist. For example, equipment for performing heat lesions is available from Radionics, Inc., located in Burlington, Mass. Radiofrequency (RF) ablation is well known and is described in medical and clinical literature. To that end, a research paper by E. R. Cosman, et al., entitled "Theoretical Aspects of Radiofrequency Lesions in the Dorsal Root Entry Zone," Neurosurgery, Vol. 15; No. 6, pp. 945–950 (1984), describing various techniques associated with radiofrequency lesions, is incorporated herein by reference. Also, by reference, a research paper by S. N. Goldberg, et al., entitled "Tissue Ablation with Radiofrequency: Effective Probe Size, Gauge, Duration, and Temperature on Lesion Volume," Acad. Radiol., Vol. 2; pp. 399–404 (1995), describes techniques and considerations relating to tissue ablation with radiofrequency energy.

In addition, a paper by S. N. Goldberg, et al., entitled "Hepatic Metastases: Percutaneous Radiofrequency Ablation with Cool-Tip Electrodes," Radiology, Vol. 205, No. 2, pp. 367–373 (1997), describes various techniques and considerations relating to tissue ablation with radiofrequency electrodes having cooled electrode tips. Cooling of the electrode can result in larger volume of RF heating due to the extension of the heating volume to greater radii away from the electrode. Cooled ablation electrodes may maintain tissue near the electrode at temperatures that are below tissue ablation temperatures.

SUMMARY OF THE INVENTION

A technique which is minimally invasive, safe, and effective for ablating large metastatic bone tumors for the purpose of destroying the tumor and for the purpose of relieving pain associated with such metastases is desirable. Accordingly, an effective technique for performing RF electrode ablation of metastatic tumors is desirable for the purpose of reducing the volume of the metastatic tumor, for killing the entire tumor volume, or at least a portion of the tumor volume, and for the alleviation of pain for the patient.

The present invention is directed towards a system and procedure for heat ablation of bone metastases through use of a probe which is advanced either percutaneously or under direct surgical approach into the bone metastasis or into peri-osseous tissue (tissue on, near, surrounding, or in the bone). The guidance of the probe into the bone metastasis can be assisted by various imaging methods is such as ultrasound, CT, MRI, stereotactic, or other imaging or image-guided system methodologies. The advantages of the present system and method reside in their combined simplicity, economy, control, consistency, enablement of good ablation position and shape, total destruction of metastatic tumor and clinical effectiveness to reduce the tumor volume. Another advantage of the present system and method is that in some cases it can provide instant pain relief for the patient who suffers from the advancement of metastatic bone tumors.

In one embodiment, the technique of the present invention involves inserting a rigid, tissue-piercing radiofrequency (RF) electrode through the patient's skin into the region of the tumor, as visualized under a CT tomographic scan. The RF electrode can be of a cooled type, as described by Goldberg, et al. in the reference above. Application of sufficient power from an RF generator connected to the electrode will deliver heat to the metastatic tumor, thereby destroying part or all of the tumor volume by reducing the tumor to a necrotic fluid mass which may be absorbed by the patient's body. The use of multiple and/or curved electrodes placed into the tumor volume can supplement the shaping of the RF ablation heat region. This application of an RF heating electrode or other type of thermal probe or pulsed RF element into the tumor, surrounding bone, or periosseous tissue can also relieve pain in accordance with the present invention.

In contrast to radiation therapy and chemotherapy, the RF electrode ablation technique is minimally invasive, simple, and well tolerated by the patient. For example, this technique may be performed when the patient is lightly sedated. The procedure can take less than an hour and is minimally invasive thereby reducing the risk of bleeding, infection, surgical complications, radiation risks, and morbidity and mortality in comparison to radiation and chemotherapy methods.

The present system and method has the further advantage in many cases of relieving the excruciating pain associated with the presence of the metastatic tumor. This pain relief can, in some cases, occur almost instantaneously with the application of the radiofrequency ablation heat. The adjunct of pain relief can instantly and dramatically improve the quality of life of the patient suffering from the metastatic bone cancer.

A further advantage of the present technique is that by use of a cooled tissue-piercing electrode, very large ablation volumes can be achieved to treat the very large volumes that are common for metastatic tumors in the bone. It should be noted that Rosenthal, et al. in the article referred to in the Background section did not contemplate the use of cooled electrodes for achieving very large ablation volumes, nor did they contemplate using thermal ablation systems and methods for the treatment of metastatic bone disease and associated pain, which is a common, invasive, and aggressive problem for patients with terminal malignant cancer.

Also, the present technique may avoid injury to surrounding tissue, in contrast to such risk of injury posed by radiation therapy. Radiofrequency ablation does not destroy red bone marrow in surrounding bones that are outside the target area (the ablation heat volume). In contrast, this is a significant problem in poorly directed X-ray radiation dosimetry. The RF ablation method enables a total kill of all or part of the tumor within the ablation volume. This volume can be graded by the surgeon by the degree of power applied and the temperature in the ablation volume.

A further advantage of the RF ablation technique is that it is repeatable. For example, in a second session, further ablation of bone tumors can be performed with relatively minimal risk to the patient.

A significant advantage of the RF ablation method for bone metastases is that it is clinically effective and economical. The procedure is relatively simple in contrast to regimes of chemotherapy and radiation therapy. It has been found to be very clinically effective at reducing metastatic tumor volumes and providing dramatic pain relief for patients suffering from this disease. The radiofrequency electrodes may be simple structures that can be manufactured and sold at economical levels, as compared to structures used with chemotherapy and radiation therapy. Further, all or part of the metastatic bone tumors may be uniformly killed by radiofrequency heating. This is not the case for radiation therapy where some tumors are not sensitive to X-rays and where dose limitations (e.g., due to the critical location of the tumor) prevent escalation of X-ray dose.

Moreover, radiofrequency ablation can be performed during the same intervention as a biopsy of a metastatic tumor, thus making the procedure even simpler because it can be performed in a single session. This has the advantage of great convenience for the patient, surgeon, and hospital, and reduces substantial management costs, operating theatre expenses, and logistics as would occur for radiotherapy and chemotherapy. The patient can undergo the radiofrequency ablation in one simple session lasting typically one hour. This is an advantage in time effectiveness compared to radiation therapy or chemotherapy, which require weeks and sometimes months of a complex regimen of applications which are expensive and inconvenient for a patient who may have to travel a significant distance to the hospital center.

Another advantage of the present invention is that it is minimally invasive and easily tolerated by the patient. Often patients with advanced cancer and bone metastases are in frail health and cannot tolerate surgery or protracted therapies. Heat ablations offer them a convenient, simple, and minimally intrusive way to handle a disease state for which there are few or no other clinical options left. The present invention can reduce the dependency of the patient on chemotherapy or pain relieving drug therapies, either of which can severely reduce the patient's quality of life.

In one embodiment of the invention, image-guided data such as CT, MR, or X-ray information is used to plan the placement of RF electrodes. This data can be used in a computer with a graphic display to visualize and plan the placement of electrodes in the bone, bone tumor or periosteum for proper ablation coverage of heat distribution. Image guidance during the electrode placement and use of a stereotactic-guided, electrode support, and/or digitizer/image-guided navigator helps in placement and control of the electrodes into or near the tumor.

DETAILED DESCRIPTION OF THE INVENTION

Figure 1:
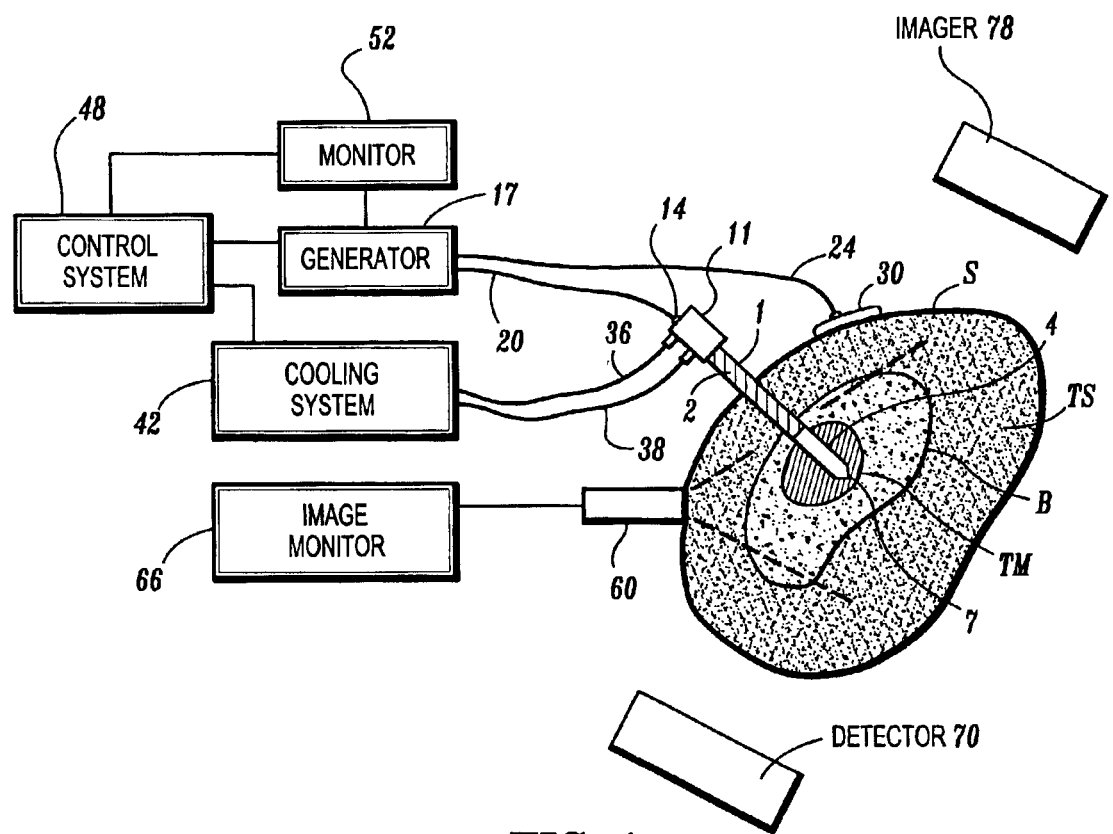
FIG. 1 shows a schematic diagram in partial sectional view of one embodiment of an electrode placed in a bone tumor together with a high frequency generator, cooling system, and monitoring in accordance with the present invention.

FIG. 1 illustrates one embodiment of a system and procedure according to the present invention comprising an electrode 1 which is inserted through the skin S of the tissue TS to penetrate a bone B in which there is a tumor (represented by the perimeter TM). This sectional view of the anatomy could be present anywhere in the body, including the limbs, pelvis, spine, skull, feet or other locations. The shaft of the electrode 1 has an insulated portion 2, as represented by the shaded area. The shaft has an exposed conductive tip 4 which, in this embodiment, has a pointed tip 7. The shaft may for example be made of a rigid metal tubing insulated by a plastic or other insulative layer 2 with a pointed structure 7 at its distal tip adapted to penetrate skin, tissue, and bone to reach the tumor TM. The length of the exposed tip 4 may be fixed, or alternatively the electrode may be adapted so that the length of the exposed tip 4 may be adjustable to accommodate the dimension of the tumor with respect to the direction of approach of the electrode 1 into the body. The pointed tip 7 may be of conical, trocar, bevel, or other type of sharp tissue-piercing, bone-piercing form. The electrode has a hub 11 which accommodates an electrical connection 14 that connects by cable 20 to a high frequency generator apparatus 17 external to the patient's body. The apparatus applies high frequency output such as radiofrequency (RF) output to the electrode tip 4. The RF output power, in turn, heats tumor tissue TM in order to kill part or all of the tumor by thermal ablation. A reference electrode 30 may be a surface type electrode that is conductively connected to the skin S. It is connected by a cable 24 to the high frequency generator 17, thereby completing the electrical RF circuit through the patient's body. In other embodiments the electrode configurations could be devised with a bipolar tip, thereby eliminating the need for a reference electrode. By reference, the paper by Cosman cited in the Background section describes configurations of electrodes including bipolar and monopolar configurations as well as typical radiofrequency generator connections.

Also shown in FIG. 1 is a cooling system 42 which is connected to the electrode by cooling cables 36 and 38. A cooling fluid from the cooling system 42 is passed through the shaft of electrode 1 to cool the electrode tip 4 during one phase of the thermal ablation process. The cooling system 42 will enable larger radiofrequency ablation volumes to be achieved compared to non-cooled electrodes. In the case of very large tumor regions TM, a cooling system 42 may suit clinical needs to properly obliterate the entire tumor or portions of the tumor. By reference, the paper by Goldberg, et al., cited in the Background section, describes the use of cooled radiofrequency electrodes.

During the RF heat ablation process, the cooling system 42 may be turned on or turned off to achieve extended or less extended heating volumes. For example, when the electrode tip 4 is cooled during RF output application, a larger lesion volume in the bone can be achieved. Alternatively if the tip 4 is not cooled during RF application, a less extended heat ablation is achieved close to the tip 4.

Also shown in FIG. 1 is a control system 48 that controls the operation of the high frequency generator 17 and the cooling system 42. In addition, a monitor (e.g., a display device) 52 can display the functions of the various elements 17, 48 and 42, as well as display parameters for each of these systems.

Also shown in FIG. 1 is an image monitor 66 coupled to an imaging apparatus 60. The imaging apparatus 60 may be, for example, an ultrasound scanner that monitors the position of the electrode 1 relative to the tissue TS and bone B.

Also shown is an imaging machine (imager 78) which may comprise a CT, MR, PET, ultrasound, X-ray, or other imaging device that may be used to determine the position of the electrode 1 in the body and/or to monitor the RF lesion ablation process. In some embodiments, the imager 78 is used in conjunction with a separate detector 70 that detects, for example, excitation in the patient's body that is induced by the imager 78 or rays from the imager 78 that passed through the patient's body.

In an embodiment where the imager 78 is an MRI scanner, the isotherm regions resulting from the RF heating process may be determined and visualized by the MRI scanner 78 in real-time or shortly after heating. This can enable visualization of the ablation process as the heat distributes into the patient's body, thereby monitoring whether the ablation has engulfed the desired portion of the tumor or peri-osteous tissue.

In another embodiment imager 78 may be a CT image scanner that is used to determine the position of the electrode placed in or near bone B and tumor TM to guide and/or confirm the electrode placements.

Alternatively, imager 78 may be an X-ray or fluoroscopic imaging apparatus. In this case, X-rays typically will pass through the body (i.e. tissue TS) and be detected by a detector 70.

In FIG. 1, the electrode 1 may be a robust and rigid electrode that is capable of piercing bone. It may comprise a metal tubular shaft 1 with a rugged, pointed tip 7. The electrode 1 may vary in dimension from a fraction of a millimeter to several millimeters in diameter, depending on the particular application. The electrode 1 may be made of robust metal tubing with appropriate wall thickness to prevent buckling or bending during penetration of tough soft tissues or the hard bone. Such tubing may be made of stainless steel or other metals. The electrode 1 could be made of a tough plastic with external metal contacts or it may consist of an insulative sheath over a metal core.

The electrode 1 may be made of MRI-compatible material which does not distort or disturb MRI imaging. The material may be selected to provide the desired degree of imaging of the probe in the MRI image data. Examples of such MRI-compatible materials are titanium, copper, various forms of stainless steel, aluminum, or other advanced alloys.

The exposed length of the tip 4 can be varied or be gauged, depending on the size of the tumor TM. Various electrodes having differing fixed lengths of exposed tip 4 can be provided to suit clinical needs. In one embodiment, the electrode 1 may consist of a cannula having an insulation portion 2 which is an independent sheath that can be moved back and forth over a metal electrode inserted into the sheath. This is used to achieve various lengths of the exposed tip as set by the clinician. By reference, various styles and constructions of radiofrequency electrodes that may be adaptable to the present invention are produced by Radionics, Inc. (Burlington, Mass.) and Radiotherapeutics, Inc. (Mountain View, Calif.).

The hub 11 may be made of radiolucent material such as plastic so that X-ray or fluoroscopic images can be taken with the hub in place to get a "needle-view" image; thereby enabling a physician to direct the probe under real-time fluoroscopic or C-arm imaging.

During the process of making a heat lesion to treat bone metastases and to treat pain associated with this cancer, exposures of heat to the bone may last for several seconds to several minutes, or even as long as a fraction or multiples of an hour. Multiple sessions may be desirable to fully encompass the tumor volume.

Figure 2:
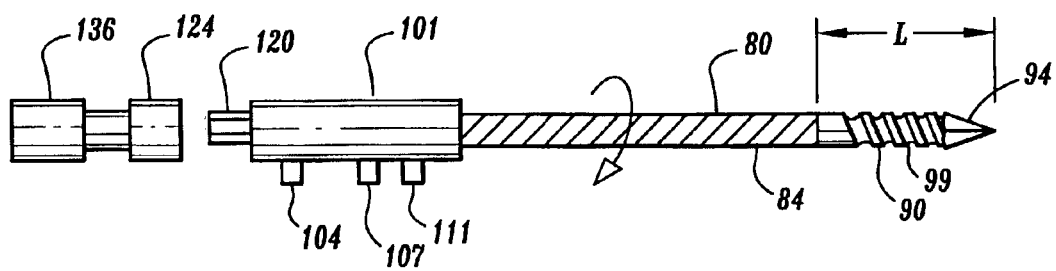
FIG. 2 shows one embodiment of an RF electrode adapted for treating bone metastases in accordance with the present invention.

FIG. 2 illustrates another embodiment of the present invention in which a rigid shaft 80 has an insulated portion 84 (represented by the hatched lines). An exposed tip 90 has length L, which may be fixed or variable to suit clinical needs. A pointed tip 94 facilitates penetration of tissue and of bone. Also shown on the tip are threaded, screw-like, augered, or corkscrew-type grooves 99 to enable a screwing or drilling type penetration into bone. The hub 101 has at least one electrical connection 104 to a generator system (as shown in FIG. 1). Hub 101 also has fluid cooling input and output channels 107 and 111. Also shown on the hub is an adapter 120 that can mate to an external driver 124 to push and/or turn the electrode shaft during penetration of tissue and bone. External driver 124 can be connected to a hand piece or to a motor drive 136 to advance the drill structure through the hard bone cortex.

Figure 3:
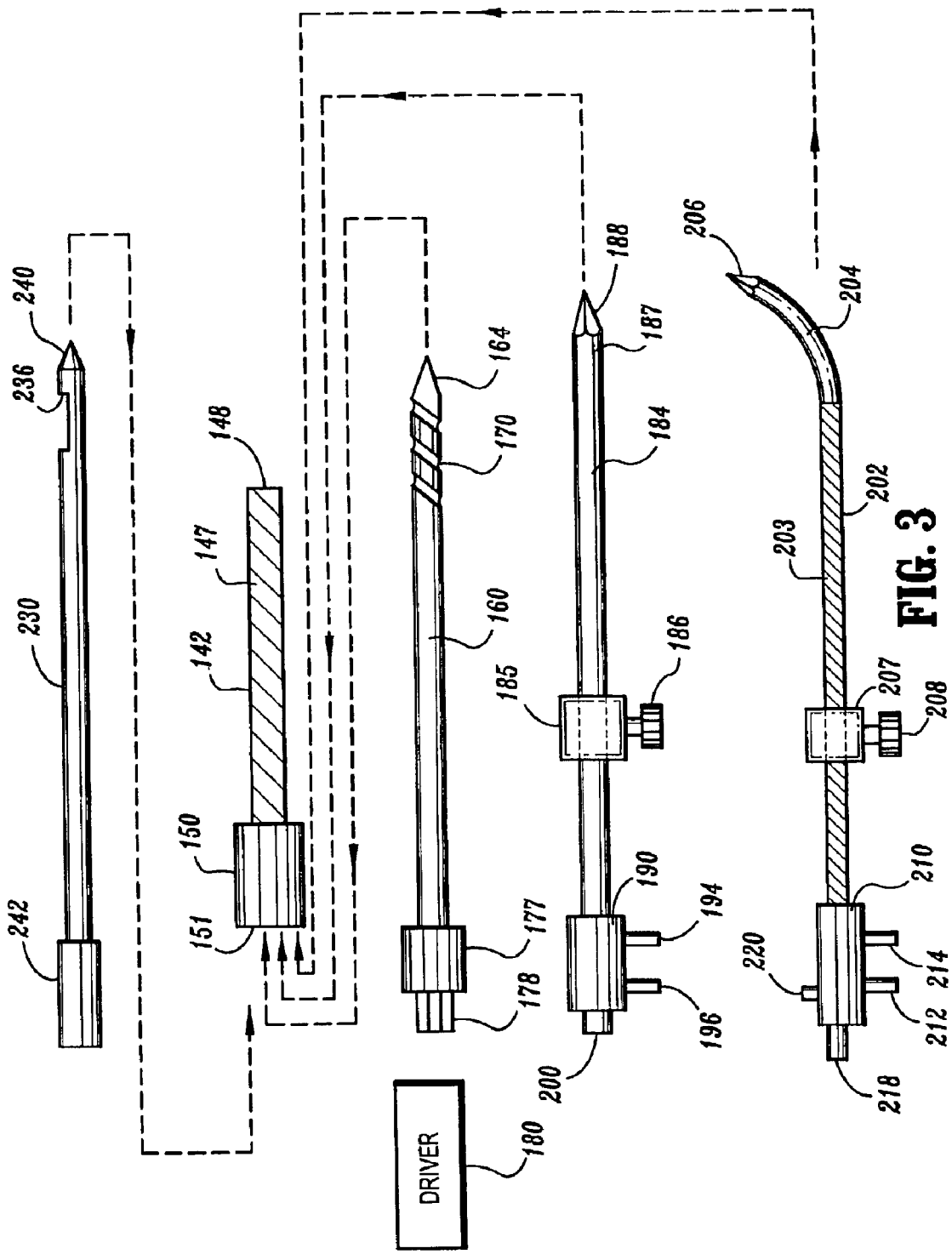
FIG. 3 shows various embodiments of a set of cannulae, stylet, biopsy device, and RF electrodes for treating bone metastases in accordance with the present invention.

FIG. 3 shows another embodiment of the present invention in which a set of tools are used to penetrate, perform a biopsy on, and heat-ablate the bony structure. A cannula 142 has an insulated area 147, indicated by the hatched lines, and an open front-facing lumen 148 at its distal end. On the cannula's proximal end there is a hub 150 which has an opening 151 on its proximal tail end. The opening 151 alternatively accepts either a stylet 160, a biopsy device 230, or various RF electrodes 184 and 202 as indicated by the dashed arrows. Stylet 160 may be a rigid metal shaft with drill or screw type structures 170 at its distal end and a robust (e.g. hardened) pointed tip 164. As in the electrodes in FIGS. 1 and 2, the distal tip 164 can take various forms such as a trocar, a drill-like point, a conical point, a cutting auger point, or other designs to penetrate bone.

On its proximal end, stylet 160 has a hub 177, with drill adaption 178. Drill adaption 178 may be, for example, a hex, square, grooved, or other type of drive adaption that accepts an external driver 180 with compatible mating shapes. For example, a drill or hand piece (driver 180) can be used to advance and drill the stylet 160 into the bone. The drill stylet 160 may then be removed from the sheath 142 and an RF electrode 184 can be inserted in its place. In one embodiment the RF electrode 184 has a depth stop 185 with a locking thumb 186 on the shaft. Thus, the degree of extension of the tip portion 187 beyond the cannula end 148 can be pre-set, determined, or changed as needed. The shaft of the RF electrode 184 may comprise a metal tubing, such as stainless steel, with a pointed tip to enable penetration of the electrode into the bone, tissue, or tumor. The electrode 184 includes a proximal hub 190 with RF connection 200 and cooling connections 194 and 196, as described above.

In one embodiment, cannula 142 may be a plastic tubing sheath with a plastic hub 150 for full CT, fluoro, X-ray, MRI, or other compatibility during imaging. Thus, even though the sheath 142 may be relatively flexible, when a rigid stylet 160 is inserted into sheath 142 the entire assembly will be sufficiently rigid to push through tissue and bone.

Also shown in FIG. 3 is a curved, flexible, or side-issuing RF electrode 202 which can be inserted into cannula 142. The electrode 202 may or may not have an insulative portion 203, indicated by the hatched lines. The electrode 202 has a distal tip 204 which may be curved, curvable, or a flexible portion, depending on the application. The distal end 204 may also have a pointed tip 206 to facilitate penetration through the bone marrow, tumor, or cortex or for pushing through soft or ligamentinous tissue. In one embodiment, the curved portion of the distal portion 204 may be a rigid and rugged permanent curve. Alternatively, distal portion 204 may have a flexible configuration so that it can be steered, pushed, or guided by the clinician through bone, tumor, joint, tissue, fissions to be positioned at various locations or paths beyond the distal opening of cannula 148. Cannula 142 may have a side curve to it which enables the flexible electrode end 204 to be urged in one direction or another. A depth stop 207 with set screw 208 enables setting of the degree of exposure of the end 204 beyond the opening 148 of cannula 142. Hub structure 210 has electrical connection 218 for the external generator, fluid cooling inputs 212 and 214, and an index marker 220 to indicate the direction of the curve of the electrode end 204. In another embodiment, multiple curved electrodes may be loaded into a common cannula to enable an "umbrella" of multiple, curved RF tips to emerge from the cannula.

The electrode 202 may be of a catheter type made of a coiled spring with or without a pre-set curve or bend in it. The electrode 202 may be flexible and directed by an internal stylet that can be inserted or withdrawn from the hub end 218. The stylet 160 may have a curved section to enable directing of the curved portion 204 to place the probe tip 206 at different points in the tissue so as to best cover the tumor or neural ablation zone. Electrode 202 may comprise tubing made of elastic or super-elastic metal such as spring-steel or nytonal tubing so that the electrode 202 can be inserted into straight segments of the cannula 142, and still describe a curved path when the curved portion 204 emerges from the opening 148 in the cannula 142. The curved probe 202 and curved portion 204 may have cooling channels within them for flow of fluids during heat ablation.

In the application of the embodiment of FIG. 3, the cannula 142 with drilling stylet 160 may be pushed through the tissue and the stylet 160 drilled into the bone or pushed directly into the bone as required by the particular clinical needs. The drill stylet 160 may then be removed from the cannula 142 and the straight radiofrequency electrode 184 or the curved radiofrequency electrode(s) 202 inserted into the cannula 142. The conductive heating tip of the electrode emerges from the distal end 148, either in a straight path or a curved path, depending on the type of electrode 184 or 202.

Connection of the high frequency generator to the electrode and delivery of generator output, voltage, current, power, or energy to the electrode will result in heating of the bone. This will have the effect of killing all or a portion of the bone tumor cells in the region of thermal ablation. The heating also may have the effect of numbing or destroying nerve cells or pain-sensitive tissue on the surface of the bone or within the bone which will help to eliminate pain associated with the metastatic bone tumors.

The cooled-tip embodiment of the present invention provides an improved method of enlarging the volume of the lesion so as to encompass all or part of the tumor and to encompass the pain or pressure sensing neurons in the endosteum of the bone, within the bone itself, or in surrounding soft or ligamentinous tissue.

Thereby the method and system of the present invention has the advantage of a minimally invasive, in some cases percutaneous, method of relieving the local pain of metastatic bone disease. As discussed above, metastatic bone cancer and multiple myeloma can affect bony structures anywhere in the body. The present invention has the advantage of being a simple-to-apply, relatively low risk, minimally invasive method of treating this highly debilitating condition of metastatic tumors in the bone and the associated pain associated with such bone tumors.

The system and method of the present invention also has the advantage that pain relief following a radiofrequency heating of a bone metastasis is, in some cases, instantaneous. The treatment may reduce the swelling of the periostial tissues associated with nerve endings that is caused by the pressure and encroachment of the cancerous tumor. The treatment also may be used to directly ablate the nerves and nerve ramifications in and/or around the bone to desensitize them against further tumor encroachment.

Other methods of heating the bone tumor and nerve cells using a probe maybe devised in accordance with the present invention. For example, probes such as in the above embodiments may use a resistive heater element. Referring again to FIG. 1, delivery of power from generator 17 to probe tip 4 may be passed through a resistive wire element such as a nichrome wire within the tip 4 to heat the tip. This hot tip may in turn heat the bone, tumor, nerve cells, or other tissue types near or in the bone to ablate a portion of the tumor and/or to reduce pain. In another embodiment, the electrode may include a microwave radiating element, and the generator may be a microwave power generator. In other embodiments, the generator may be a source of ultrasonic or laser energy and the probes consist of compatible applicators that deliver the energy to the bone tissue region to produce the ablation effect.

FIG. 3 also illustrates a biopsy tool 230 which can be inserted into the cannula 142. A biopsy may precede use of the radiofrequency cannulae. For example, in one method, the cannula 142 with stylet 160 or with biopsy cannula 230 are introduced percutaneously through the skin to penetrate the bone by drilling or tapping through the bone cortex. A bone biopsy can then be done by use of the tool 230 through the cannula 140. By reference, bone biopsy needles are commonly known in the orthopedic area. The biopsy tool 230 in FIG. 3 has a cutting tip 236, which extends beyond the front-facing lumen 148 of cannula 142. The biopsy tool 230 also has a pointed tip 240 for penetrating bone and bone marrow. Hub 242 enables the biopsy tool to be manipulated so as to core out or extract a tissue sample of bone. If the tissue sample is analyzed and found to be malignant, then the RF cannulae 184 or 202 can be placed through the cannula 142 to perform a radiofrequency lesion operation.

Figure 4:
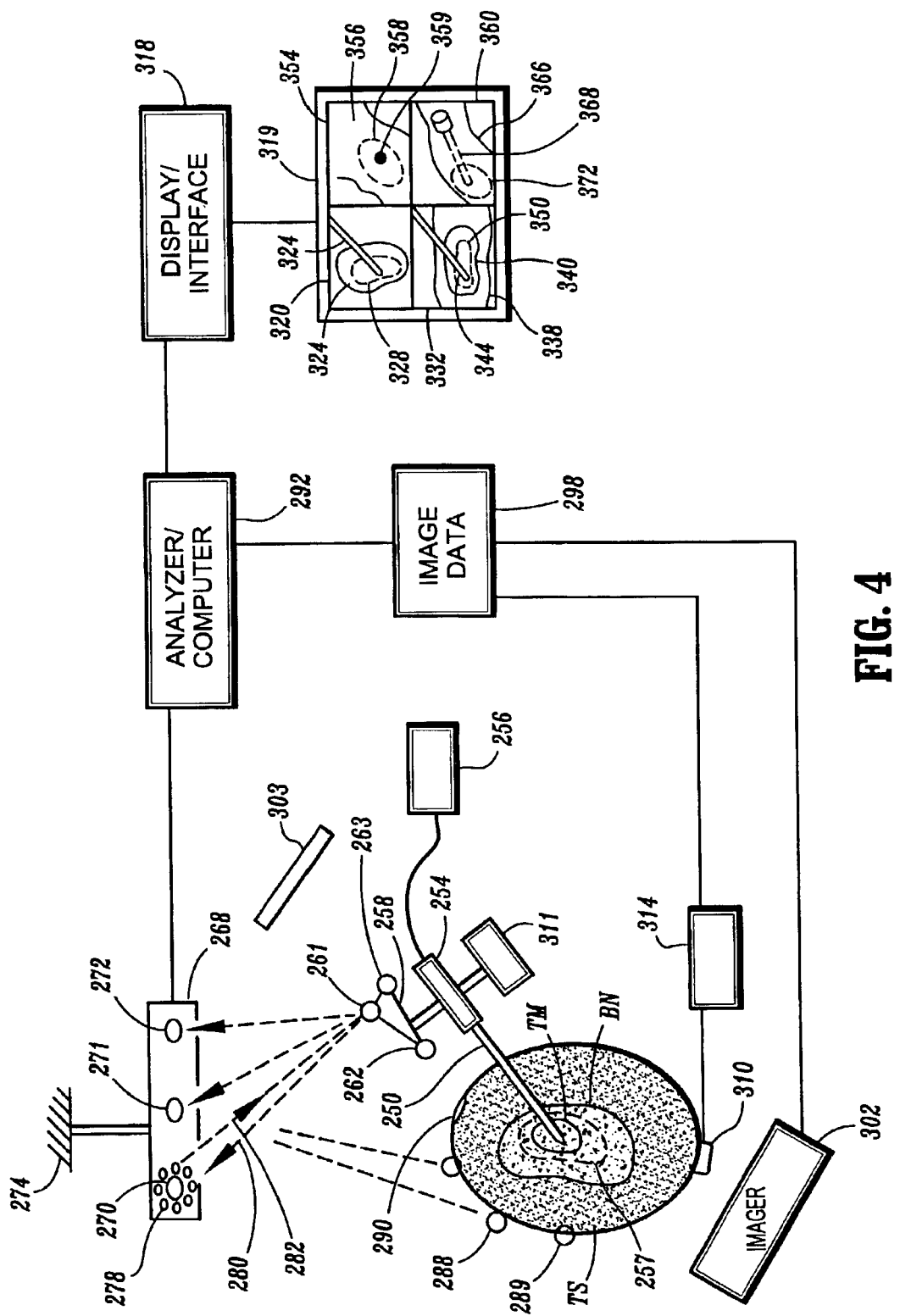
FIG. 4 shows a schematic diagram of one embodiment of a navigation guidance system used with a bone metastasis ablation probe and imaging in accordance with the present invention.

FIG. 4 shows another embodiment of an ablation needle and an image guided navigation system in accordance with the present invention. The ablation needle (applicator 250) is inserted into the tissue TS of the patient's body, into the bone BN, and into a tumor volume TM. The hub of the ablation cannula 254 is attached to a navigator system 258, which in this case may include light source objects 261, 262 and 263 such as light-emitting diodes (LEDs) or light reflecting objects. The objects 261, 262 and 263 are defined in an array, geometric pattern, or structure that is identifiable by camera system 268 so that the objects 261, 262 and 263 may be tracked in the three dimensional space of the operating theatre.

Camera system 268 comprises one or more cameras, such as cameras 270, 271 and 272, which view the surgical field and track the probe 252 by detection of an object, such as 261. The camera system 268 may have light-emitting sources (e.g., LEDs) 278 that emit rays 282 that are, in turn, reflected (rays 280) from the reflective objects such as 261 back to the cameras 270, 271 and/or 272 to track the position of the object 261, and therefore the position of the probe 250. By reference, the optical tracking system of U.S. Pat. No. 5,662,111, incorporated herein by reference, illustrates the use of optical tracking of surgical tools in the operating room.

Other objects such as 288 and 289, and so on may be placed on or in the patient so they may be tracked by camera system 268 to provide a dynamic referencing of relative movement of the patient's anatomy relative to the surgical probe 250. By reference, the dynamic reference system of U.S. Pat. No. 5,662,111 illustrates dynamic referencing of an instrument relative to the patient's body for continuous update of registration. The objects such as 288 may take various forms, including a reflective sphere or an LED, or as illustrated by object 290, a strip or disc or other geometric shape of a light-emitting or light-reflecting object.

The signal data from the camera system 268 may be sent to an analyzer, synthesizer, or computer 292 to provide information correlating the position of the probe relative to the patient's anatomy. This information can be transformed to a format suitable for display, then coupled to an appropriate display interface (indicated by the processing component 318 in FIG. 4). Display/interface 318 may comprise a computer graphic workstation that uses an associated display device 319 to display the position of the probe 250 relative to the anatomy TS and the bony tumor TM.

In one embodiment, image data also may be sent to the computer 292. The image data 298 originates from an imaging system (components 302 and 303) which generates CT, MR, PET, X-ray, fluroscopic, or other image scanning data before or during the ablation procedure. Data from an imager 302 may be temporarily stored in a data memory (e.g. random access memory), as represented by block 298, and transferred to the computer 292 as necessary.

Also shown in FIG. 4 are other types of navigating devices 310, along with their associated synthesizers 314. The navigator system 310 and 314 may comprise a magnetic device, a solid state device, or a radiofrequency tracking device which can track the position of an element 311 attached to the probe 250 to provide image-guided surgery tracking and navigation during surgery in a similar manner as discussed above. Again, image data from the navigator system 310 and 314 may be stored in memory 298.

The computer graphic display 319 may display the updated position data for the probe 250 as it approaches and penetrates the patient's tissue TS and bone BN. The various examples of navigator systems described above can provide data that describes the position of on the probe with respect to image data 298 from image scanners such as 302 and 303. This position data describes the position of the probe with respect to image data 298 acquired prior to the procedure or with respect to image data 298 that is acquired at the time of the procedure. In the display windows of display 319, there is an image window 320 which shows representations 324 and 328 of the tissue TS and the bone BN, respectively, as defined by one sectional view of the image data. Also displayed in window 320 is a representation 324 of the probe 250. These representations may be determined by the navigating tracking systems such as the camera system 268 and electromagnetic tracking system 314. Therefore, in one sectional view, the position of the probe (electrode) relative to the bone and the bony tumor may be displayed.

In window 332 of the display 319, another slice section through the anatomy is displayed including representations of a profile of the tissue 338, the bone 340, and, in this figure, a dashed line 350 represent an outline of the tumor. In this case, outlines of these anatomical structures may have been preprocessed from the image data 298. The probe 250 is shown as represented by the element 340 as it approaches the tumor.

Another window 354 in the display 319 may represent a "probe's-eye-view" or reconstructed view of the same anatomy. Here, the probe appears as a dot-like structure 359 in its approach to the tissue 356 and tumor 358.

The window 360 of display 319 provides a three-dimensional rendering of the probe 368 as it approaches the tissue 366 and the bone or tumor 372. This perspective assists the physician in guiding the actual electrode 250 into the proper target region.

Figure 5:
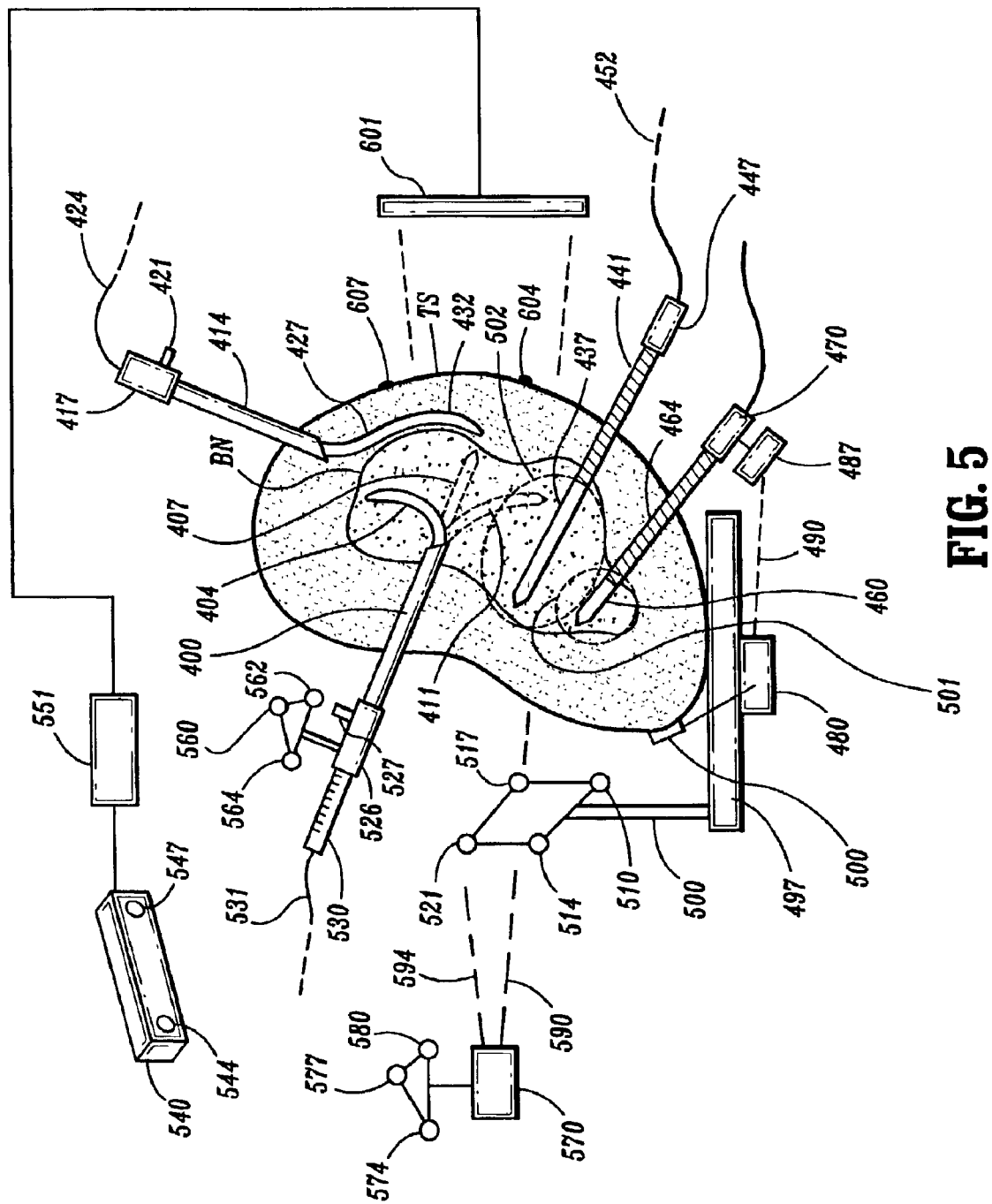
FIG. 5 shows various probe geometries with navigation and imaging guidance in accordance with the present invention.

Referring to FIG. 5, another embodiment of the system and method of the present invention is shown wherein multiple electrodes of various forms are used to approach a bone and a bony tumor to ablate the tumor and/or relieve the associated pain. An electrode system comprises a shaft 400 that is inserted into the tissue TS and into or proximating the bone BN. As discussed above, the shaft 400 may comprise a cannula through which can be passed a high frequency electrode with either straight tip 407 or curved tip 404 or 411. In one alternative embodiment the electrode tip shape 407 (illustrated by the dashed lines) comprises an electrode which emerges substantially straight out of the distal end of the cannula 400.

The curved portion of the electrode 404 is a high frequency conductive exposed electrode tip which emerges from the distal end of cannula 400 and is configured in a curved shape. This may be achieved by having a permanent curve on an electrode which is passed through the cannula 400 such that as it emerges from the distal end it arcs in a circle. Alternatively, the electrode may have a flexible but steerable tip which can define more or less of an arc, as set by the physician, as it emerges from cannula 400. A spring-like electrode 404 can be devised which has a permanent arc shape to it, and yet can be straightened out to be pushed through the cannula 400 so that it emerges in a predisposed arc shape such as 404. Alternatively, portion 404 may be a curved tubing or wire, or a coil-plus-internal curved wire assembly so that it emerges as an arced curve from cannula 400. Elastic metals or coils such as nitinol can be used for this purpose. In this way, the electrode 404 can reach remote portions of the bone or bony tumor or tissue near the bone to extend or contour the heat ablation region.

A steerable or flexible electrode can be directed in any azimuthal direction by rotating the hub 526 to orient the electrode in different positions. This is illustrated, for example, by the curved or arced electrode tip 411 shown in dashed lines. In this way, a large region surrounding the distal end of the cannula 400 can be exposed to the heat ablation procedure.

FIG. 5 also shows another embodiment of the electrode comprising a cannula 414 which is inserted near to the bone BN and can be used to produce heat lesions near the peri-osteum or bone surface. A flexible RF tip 427 emerges from the distal tip of cannula 414 and can follow the contour of the bone BN when pushed into the peri-osteal region from a desired direction, as illustrated by the portion of the tip 432. During RF heating, the nerve enervating the bone at its surface can thereby be effectively ablated to relieve pain associated with peri-osteal tissue, as for example caused by the pressure of a tumor.

FIG. 5 also shows another embodiment of the present invention in which multiple electrodes are positioned as an array so that the ablation volume covers the tumor volume. Electrodes 441 and 464, in this example, are straight electrodes. They are placed within the bone BN, and their exposed tips 437 and 460, respectively, are of the appropriate length and positioned to effectively cover a portion of the tumor by appropriate ablation isotherms (as represented by dashed lines 501 and 502).

Any number of such electrodes may be used, as needed, and their position may be pre-planned by a computer analysis of the three-dimensional geometry of the bone and the tumor. That is, a plan of the number of electrodes and their position can be developed by a computer for optimal placement of electrodes. The electrodes can thereafter be positioned in the bone using on-line image guidance such as X-ray or ultrasound or by using stereotactic navigation such as an electrode guidance system or a three-dimensional digitizer, as discussed above.

For example, the electrodes may be placed by a stereotactic frame or stereotactic navigator. For electrode 400, a set of light-detectable objects 560, 562, and 564 are attached to hub 526. The objects 560, 562 and 564 are detected and tracked by camera system 540, which comprises one or more cameras such as 554 and 547. By reference, the Optical Tracking System of Radionics, Inc., Burlington, Mass., tracks instruments in a medical setting. An example of tracking a probe in conjunction with computer visualization is given in connection with FIG. 4 above. The element 551 represents the processing components for analyzing computer image data, the imaging machines, the displays, and the interfaces as described above.

FIG. 5 also illustrates the use of an imaging machine 570 which could be, for example, an X-ray machine, a fluoroscopic machine, a digital CR machine, and so on. For example, the imaging machine 570 may emit imaging X-rays indicated by the dashed lines 590 and 594 that project the patient's body and the target region onto a detector screen 601. The imaging data from the detector screen 601 can be sent to the complex of analyzers, computers, and displays 551.

Images from the screen 601 may then be image fused or merged with two-dimensional reconstructions from three-dimensional image scan data such as CT, MR, PET, etc. taken at a different time or taken simultaneously with 2-D (two-dimensional) X-ray data. As a result, structures in 3-D (three-dimensions) can be correlated with the structures detected in two dimensions by the screen 601. Index marks 604 and 607 on the surface of the patient's skin can serve as fiducial points to correlate three-dimensional data taken by CT or MR machines with the markers 604 and 607 and in place with the two-dimensional X-ray data taken by the X-ray machine 570 and detector screen 601. Another set of indices 510, 514, 517, and 521 are shown affixed to a structure 500 that is connected to a table 497 that supports the patient. Detecting the projections of the markers 604 and 607 or of other markers on the structure upon the X-ray screen 601 can serve to correct for movement of the patient's tissue TS, or bone BN during the procedure. The markers 510, 514, and 517, and 521 also may be detected dynamically by camera system 540 to verify the relative positions of the imaging system 570 and the patient's body and the electrodes. Thus the entire system of components can be tracked and navigated in three dimensions so as to guide the electrode based on multi-modal imaging data into the appropriate target volume within the bone.

Since the bone is a complex, three-dimensional shape, as is the bone metastasis within it, use of such multi-modal three-dimensional imaging with image guidance and navigation could assist in efficient placement of electrodes and thermal ablation volumes. By reference, the Optical Tracking System Navigator of Radionics, Inc. uses cameras and dynamic referencing techniques.

Figure 6:
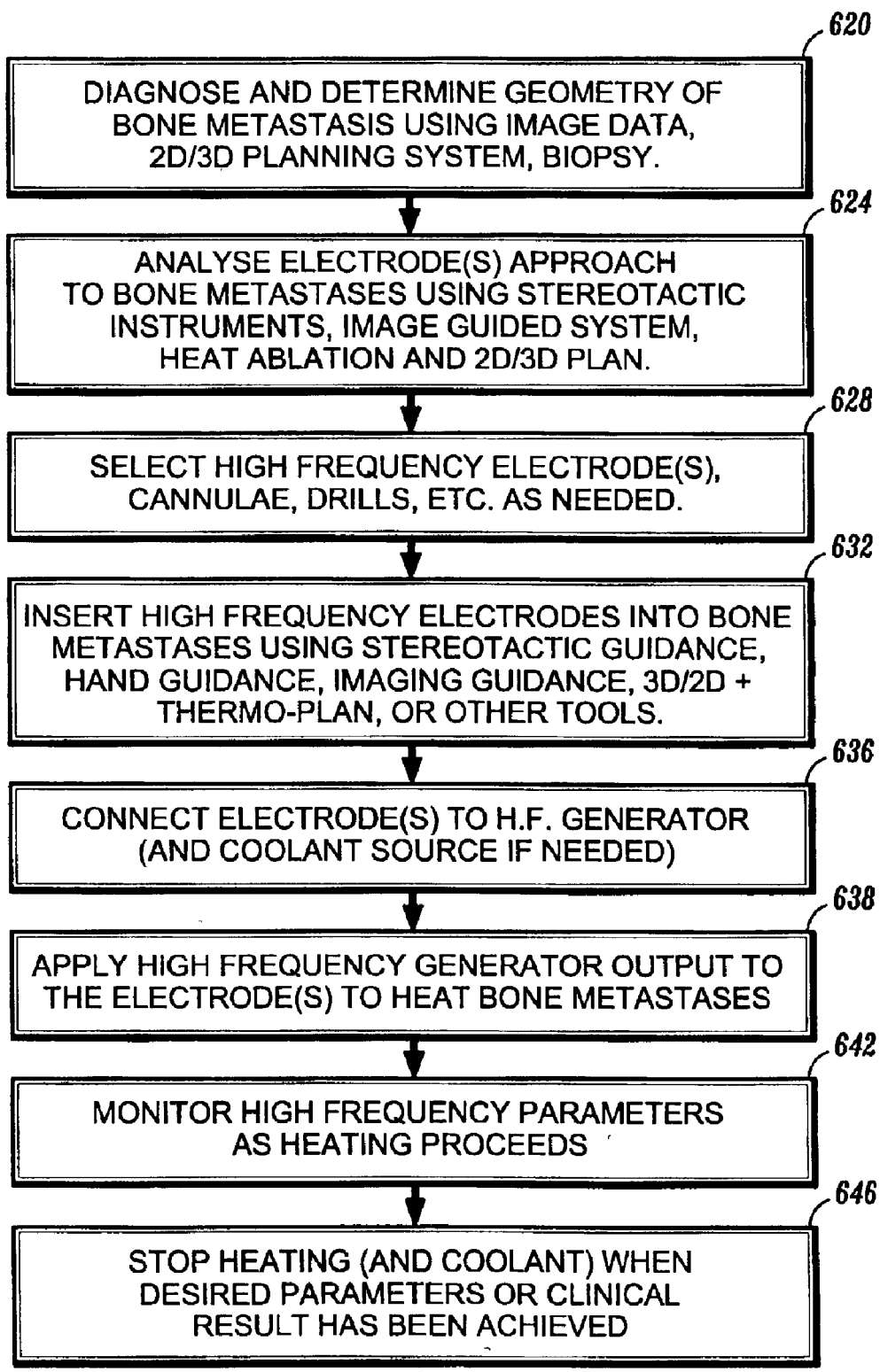
FIG. 6 shows a flow chart of a process that may be employed in operating a system to treat bone metastases in accordance with the present invention.

FIG. 6 shows a process in accordance with the present invention involving steps for use of the system for RF pain and tumor therapy of bone metastases.

From imaging of the bone or from biopsy diagnosis, a selection of the appropriate radiofrequency electrode geometry can be made (step 620). This could include an analysis on a 3-D computer workstation of image data to determine the location, size, and geometry of the bone and bone metastasis as well as the orientation of the bone metastasis relative to the external anatomy of the patient's tissue.

Analysis of the electrodes' approach to the bone and bone tumor is based on image data or other information (step 624), as indicated in the embodiment of FIG. 6. Historical, real-time image data, in conjugation with an image-guided surgery system or stereotactic system, may be used to navigate the electrode into the appropriate position through the tumor. Analysis of several positions or passes of the electrode may be made, and several heat lesion sequences may be carried out to cover the entire volume or multiple bone metastases. The electrode may be placed in the periosteum of the bone or may be navigated around the bone as appropriate according to clinical needs. A heat ablation plan may be prepared using a computer workstation based on 3-D image data and analysis of where the electrode or electrodes will be placed. A compound process of ablation of the tumor directly within the tumor interior as well as ablation of regions of bone peri-osteum near the tumor may be planned.

Once the pre-plan of step 624 has been done, the physician selects the heating probes and/or high frequency electrode or electrodes, cannulae, drill, biopsy sets, etc. in accordance with the present invention (step 628). The selected cannulae, biopsy needles, and high frequency electrodes can then be placed into the bone metastasis using stereotactic guidance, hand guidance, image guidance by a stereotactic navigator, or use of other tools and imaging devices such as fluoroscopic scanning or direct CT, MR, or PET imaging (step 632). Once each electrode has been placed in the tumor, each electrode is connected to the high frequency generator and, in the situation when interior cooling of an electrode is indicated, the cooling system is connected to the electrode (step 636).

Output from the high frequency generator can then be applied to the electrode or electrodes to heat the bone metastasis or other regions of the bone associated with a pain syndrome (step 638). During this process, the parameter outputs of the high frequency generator can be monitored and displayed on the generator or computer planning system as need requires (step 642). When the clinician has determined that adequate heat ablation and associated cooling process has been performed, and the clinical results are satisfactory, the process of heat ablation can be terminated and the electrode system removed from the patient (step 646).

As will be apparent to those skilled in the art, the system and method may take many forms, with multiple variations.

As examples, the electrode geometry configuration, length, and tip exposure may take many forms to suit clinical needs in accordance with the present invention. Various high frequency or other power generators may also take various forms with display, computer controls, and coupling to the image-guided system. Multiple arrays of electrodes may be used to cover the extent of the tumor volume in bone. Parallel arrays of electrodes may be implanted under image-guided surgery to quantitatively cover the extent of an irregular or large bone metastatic tumor. The electrodes may be placed one by one in a parallel array or non-parallel array for this purpose. Introduction cannulae may be used in multiple places, and radiofrequency electrodes can be placed individually or in unison into these cannulae for the purpose of obliterating the tumor. Other ablation probes and generators can be used in the embodiments of FIG. 6 and the other figures above in place of the high frequency electrodes and generator, including resistive heating probes, laser probes, ultrasound probes, and associated generators.

In view of these considerations, and as will be apparent by persons skilled in the art, implementations and systems should be considered broadly and with reference to the claims set forth below:

What is claimed is:

1. A system for treating a cancerous bone tumor or pain associated with a bone tumor in the body of a patient, comprising:

a cannula adapted to be inserted into the bone tumor, the cannula including a tubing and a removable stylet for insertion into the bone tumor;

a probe adapted to be passed through the cannula and into the bone tumor when the stylet is removed from the cannula;

an external apparatus to apply power to the bone tumor through the probe;

a cooling system with a cooling connection to the probe for delivery of cooling fluid to at least a portion of the probe; and an image-guided navigation system for controlling the position of the probe with respect to the bone tumor, the image-guided navigation system including, a camera system, at least one object attached to the probe and at least one object attached to the body of the patient, wherein each object is detectable by the camera system for generating positional information of each object, and a computer for receiving positional information of each object and providing information correlating the position of the probe relative to the body of the patient.

2. The system of claim 1 wherein the cannula further comprises a detachable biopsy device adapted to be passed through the cannula when the stylet is removed so that a biopsy of the bone tumor can be taken prior to or during the application of power to the bone tumor for treating the tumor.

3. The system of claim 1, further including a biopsy device adapted to be passed through the tubing when the stylet is removed so that a biopsy of the cancerous bone tumor can be taken prior to insertion of the high frequency electrode into the tubing.

4. The system of claim 1, wherein the probe includes a resistive heating element and the external apparatus includes a power source to supply current to the resistive heating element through the connection.

5. The system of claim 1, wherein the exposed conductive tip includes a straight portion that emerges from the distal end opening of the tubing in a direction substantially parallel to the direction of the tubing.

6. The system of claim 1, wherein the exposed conductive tip includes a curvable portion that is adapted to emerge from the distal end opening of the tubing along a curved path.

7. The system of claim 1, wherein the image-guided navigation system further includes an imaging system.

8. The system of claim 7, wherein the computer receives image data from the imaging system for providing information correlating the position of the probe relative to the body of the patient.

9. The system of claim 7, wherein the imaging system is selected from a group consisting of: CT, MR, PET, and X-ray.

* * * * *